United States Patent
Smith

(10) Patent No.: US 10,393,680 B2
(45) Date of Patent: Aug. 27, 2019

(54) X-RAY SIDESCATTER INSPECTION OF LAMINATES

(71) Applicant: The Boeing Company, Chicago, IL (US)

(72) Inventor: Nathan R. Smith, Melbourne, FL (US)

(73) Assignee: The Boeing Company, Chicago, IL (US)

( * ) Notice: Subject to any disclaimer, the term of this patent is extended or adjusted under 35 U.S.C. 154(b) by 183 days.

(21) Appl. No.: 15/408,615

(22) Filed: Jan. 18, 2017

(65) Prior Publication Data

US 2018/0202949 A1  Jul. 19, 2018

(51) Int. Cl.
*G01N 23/00* (2006.01)
*G01N 23/20008* (2018.01)

(52) U.S. Cl.
CPC ... *G01N 23/20008* (2013.01); *G01N 2223/05* (2013.01); *G01N 2223/052* (2013.01); *G01N 2223/50* (2013.01); *G01N 2223/5015* (2013.01); *G01N 2223/615* (2013.01); *G01N 2223/648* (2013.01)

(58) Field of Classification Search
CPC ............ G01N 2223/05; G01N 2223/615
See application file for complete search history.

(56) References Cited

U.S. PATENT DOCUMENTS

| 5,642,394 | A | * | 6/1997 | Rothschild | ............ G01N 23/10 378/57 |
|---|---|---|---|---|---|
| 2003/0016783 | A1 | | 1/2003 | Grodzins et al. | |
| 2016/0252468 | A1 | | 9/2016 | Lou et al. | |

OTHER PUBLICATIONS

European Search Report; Application No. 17203712.9-1003; dated Jun. 14, 2018.
Pauli Vaara et al; Technology Survey on NDT of Carbon-fiber Composites; Jan. 1, 2012.
European Office Action; Application 17203712.9-1001; dated May 20, 2019.
Poranski Chet F et al; X-ray backscatter tomography for nondestructive evaluation at the Naval Research Laboratory; Visual Communications and Image Processing; Jan. 20, 2004 San Jose.

* cited by examiner

*Primary Examiner* — Dani Fox
(74) *Attorney, Agent, or Firm* — Duft & Bornsen, PC

(57) ABSTRACT

Systems and methods are provided for detecting gaps in composite parts. One method includes radiating a beam of x-rays in a firing direction towards surface of a multi-layer Carbon Fiber Reinforced Polymer (CFRP) part, acquiring data indicating intensity of sidescatter radiation received at an x-ray detector that extends along the CFRP part in the firing direction, and examining the acquired data for gaps at the CFRP part based on differences in intensity indicated by the data.

23 Claims, 10 Drawing Sheets

X-RAY SIDESCATTER INSPECTION OF LAMINATES

FIELD

The disclosure relates to the field of composite materials, and in particular, to inspection of composite materials.

BACKGROUND

Composite parts, such as those made from Carbon Fiber Reinforced Polymer (CFRP), are made from multiple layers of composite material which are cured together to form a monolithic integral part. After curing has been completed, the part may be fastened to other composite parts in order to form a larger structure. For example, a composite skin of an aircraft may be fastened to support structure of the aircraft in order to form a portion of an airframe of the aircraft.

Inspection of composite parts for defects is complicated by the fact that the interiors of composite parts are not exposed for viewing. Thus, the internal composition of a composite part cannot be determined with the naked eye. This means that it is not possible to visually inspect a composite part in order to detect delaminations between layers of the composite part. Thus, technicians continue to seek out enhanced systems which enable rapid inspection of the internal composition of composite parts.

SUMMARY

Embodiments described herein provide for systems and techniques which utilize sidescatter x-ray imaging to inspect a composite part for delaminations between layers and/or voids. Both are referred to collectively herein as "gaps." These techniques enable, for example, the detection of delaminations at a hole drilled into a composite part, or the inspection of a side of a composite part. Furthermore, since these techniques perform imaging based on sidescatter x-ray radiation (e.g., as opposed to ultrasound or backscatter x-ray imaging), they are capable of detecting delaminations at specific locations along the entire thickness of the composite part, regardless of whether there are multiple delaminations along the thickness of the composite part. Hence, unlike ultrasound imaging which can detect only one delamination at a time along a thickness of a part, the techniques described herein provide a substantial benefit in that they are capable of detecting multiple delaminations along a thickness of a part at once (e.g., in a single image).

One embodiment is a method. The method includes radiating a beam of x-rays in a firing direction towards surface of a multi-layer Carbon Fiber Reinforced Polymer (CFRP) part, acquiring data indicating intensity of sidescatter radiation received at an x-ray detector that extends along the CFRP part in the firing direction, and examining the acquired data for gaps at the CFRP part based on differences in intensity indicated by the data.

A further embodiment is another method. The method includes identifying a region for inspection at a multi-layer Carbon Fiber Reinforced Polymer (CFRP) part, drilling a hole that penetrates multiple layers of the part in the region, inserting an x-ray detector into the hole and radiating a beam of x-rays in the firing direction. The method also includes receiving sidescatter radiation at an x-ray detector as the beam penetrates the part, acquiring data indicating intensity of sidescatter radiation received at the x-ray detector, and examining the acquired data for gaps at the CFRP part based on differences in intensity indicated by the data.

A further embodiment is a system. The system includes an x-ray source that radiates a beam of x-rays in a firing direction towards a surface of a multi-layer Carbon Fiber Reinforced Polymer (CFRP) part for inspection, an x-ray detector at the part that extends along the firing direction and receives sidescatter radiation as the beam penetrates the part, and a controller that acquires data generated by the x-ray detector, and examines the acquired data for gaps at the CFRP part based on differences in intensity indicated by the data.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
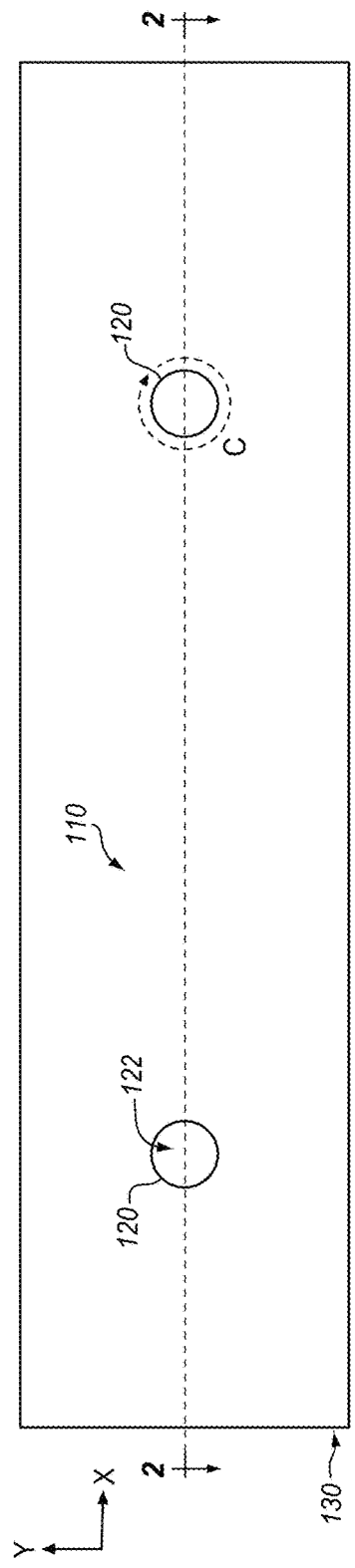
FIGS. 1-2 are diagram of a composite part that includes multiple holes in an exemplary embodiment.
Figure 2:
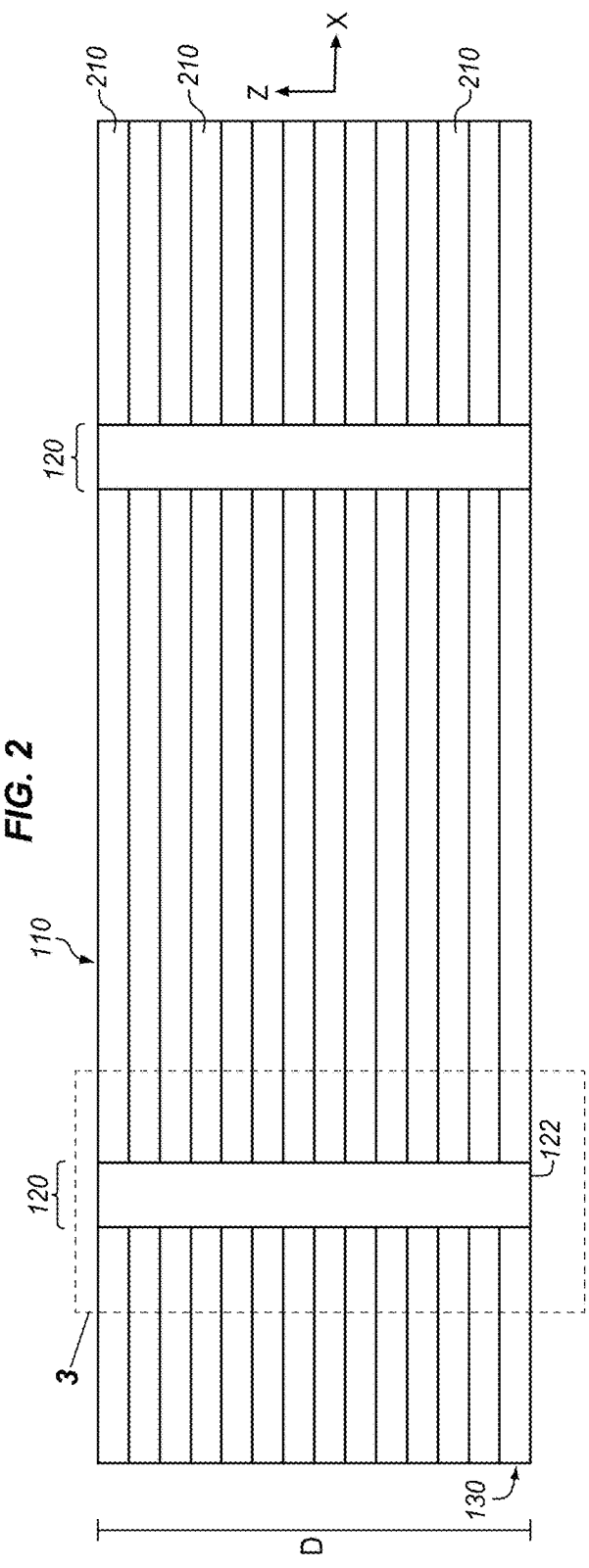

FIGS. 1-2 are diagrams of a composite part 100 that includes multiple holes 120 in an exemplary embodiment. Specifically, FIG. 1 is a view of an upper surface 110 of part 100, while FIG. 2 is a section cut view of FIG. 1 indicated by view arrows 2 of FIG. 1. Part 100 may comprise, for example, a multi-layer Carbon Fiber Reinforced Polymer (CFRP) sample. FIG. 1 illustrates that holes 120 include volumes of space 122 which penetrate through surface 110. FIG. 2 illustrates that each hole 120 continues depthwise through a thickness of part 100 (i.e., downward along the Z axis), penetrating multiple individual layers 210 from which part 100 is made. In this embodiment, each layer 210 of part 100 comprises a set of carbon fiber strands which run parallel (e.g., along the XY plane) and are held in place by a matrix of cured polymer resin. Part 100 further comprises side 130, at which part 100 terminates. Holes 120 are illustrated as having a circumference C and a depth D.

Figure 3:
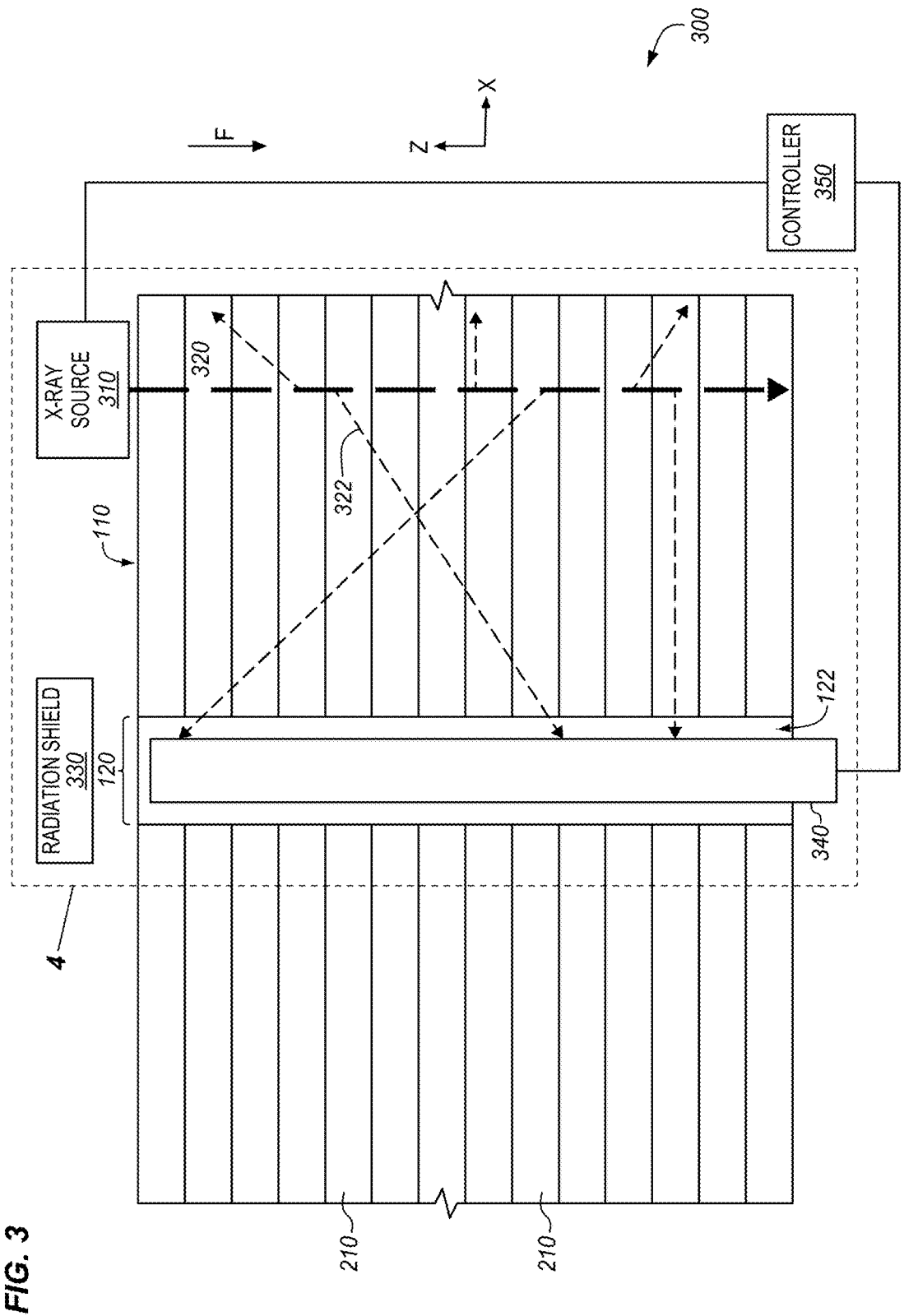
FIG. 3 is a diagram illustrating a sidescatter x-ray imaging system that inspects a hole in a composite part in an exemplary embodiment.

FIG. 3 is a diagram illustrating a sidescatter x-ray imaging system 300 that inspects a hole in a composite part in an exemplary embodiment. In this embodiment, FIG. 3 illustrates region 3 of FIG. 2, and system 300 has been placed at region 3 in order to image part 100 of FIG. 1 for delaminations. FIG. 3 illustrates that in this embodiment, system 300 includes x-ray source 310, which fires an x-ray beam 320 through the thickness of part 100. That is, x-ray source 310 radiates (e.g., fires) beam 320 through layers 210 of part 100 in a firing direction F, for example in the negative Z direction. Beam 320 may strike a 360° arc/area surrounding the entire circumference of hole 120, or may strike part 100 along a side of hole 120. As beam 320 penetrates through layers 210, a fraction of x-ray energy in beam 320 is reflected by the atoms of part 100. This attenuates the intensity of beam 320 as beam 320 penetrates part 100. Some of the reflected x-ray energy in beam 320 is directed sideways, resulting in sidescatter radiation 322. X-ray source 310 may comprise an x-ray tube, laser, synchrotron, cyclotron, or other suitable device which radiates x-rays in a controllable manner.

X-ray detector 340 absorbs sidescatter radiation 322 in order to generate an x-ray image. X-ray detector 340 may be designed to absorb sidescatter radiation 322 coming from just one direction (e.g., received along the X direction), and may even be implemented as a circumferential sensor that measures sidescatter radiation received along an entire circumference of hole 120. X-ray detector 340 may be implemented as a direct semiconductor detector, as a digital x-ray detector that stores intensity information as data in memory, as a cylindrical segment of x-ray film, etc.

System 300 further includes radiation shield 330, and controller 350. Although x-ray source 310 is shown as being located almost in contact with surface 110, x-ray source 310 may be located feet or meters away from surface 110. Radiation shield 330, which is placed between x-ray detector 340 and x-ray source 310, prevents beam 320 from directly striking detector 340, which would hinder the ability of x-ray detector 340 to monitor sidescatter radiation 322. Controller 350 manages the operations of x-ray source 310 and/or x-ray detector 340. For example, controller 350 may manage the timing, intensity, and/or shape of beam 320 generated by x-ray source 310. Controller 350 may further manage timing to control when x-ray detector 340 records data pertaining to sidescatter radiation 322. Controller 350 may be implemented, for example, as custom circuitry, as a hardware processor executing programmed instructions, or some combination thereof.

Figure 4:
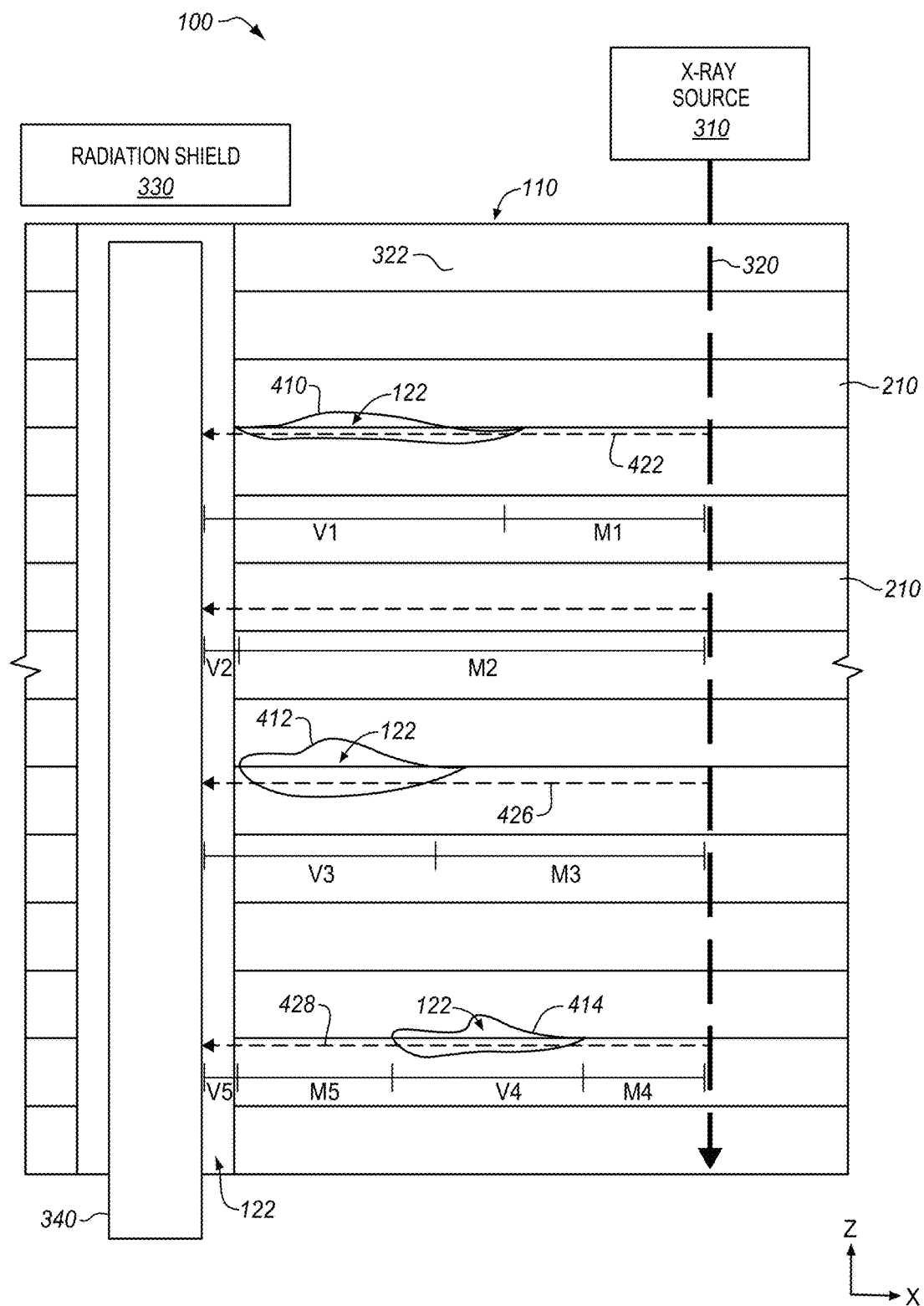
FIG. 4 is a zoomed in view of sidescatter radiation from a beam of x-rays penetrating through a composite part that includes delaminations in an exemplary embodiment.

FIG. 4 is a zoomed in view of sidescatter radiation from a beam 320 of x-rays penetrating through a composite part that includes delaminations in an exemplary embodiment. FIG. 4 corresponds with region 4 of FIG. 3. According to FIG. 4, composite part 100 includes multiple gaps 410414 at which layers 210 have become partially disbonded, resulting in undesirable volumes of space 122. Sidescatter radiation 322 passes through gaps 410-414. In particular, sidescatter x-rays 422, 424, 426, and 428 of sidescatter radiation 322 are illustrated. Each of these sidescatter x-rays proceeds in substantially the negative X direction. Other sidescatter x-rays may proceed in directions that are not aligned with X or do not otherwise travel horizontally through part 100. However, x-rays that are reflected indirectly towards x-ray detector 340 travel longer distances through part 100 and therefore are attenuated more than sidescatter x-rays 422, 424, 426, and 428 by the time they strike x-ray detector 340. Hence, sidescatter x-rays 422, 424, 426, and 428 (and other horizontally oriented sidescatter x-rays that directly strike x-ray detector 340) have a greater influence on intensity data generated by x-ray detector 340 than do x-rays which are reflected indirectly towards x-ray detector 340. This insight is relevant because gaps 410-414 at composite part 100 extend horizontally and are separated vertically. Thus, sidescatter x-rays 422, 424, and 426 are more likely to experience a change in intensity due to the presence of gaps 410-414 than sidescatter x-rays that are not horizontally oriented. This technique may further be used to detect voids that are not at the border/bond between two layers, but that exist for example as pockets of gas within a composite part.

Figure 5:
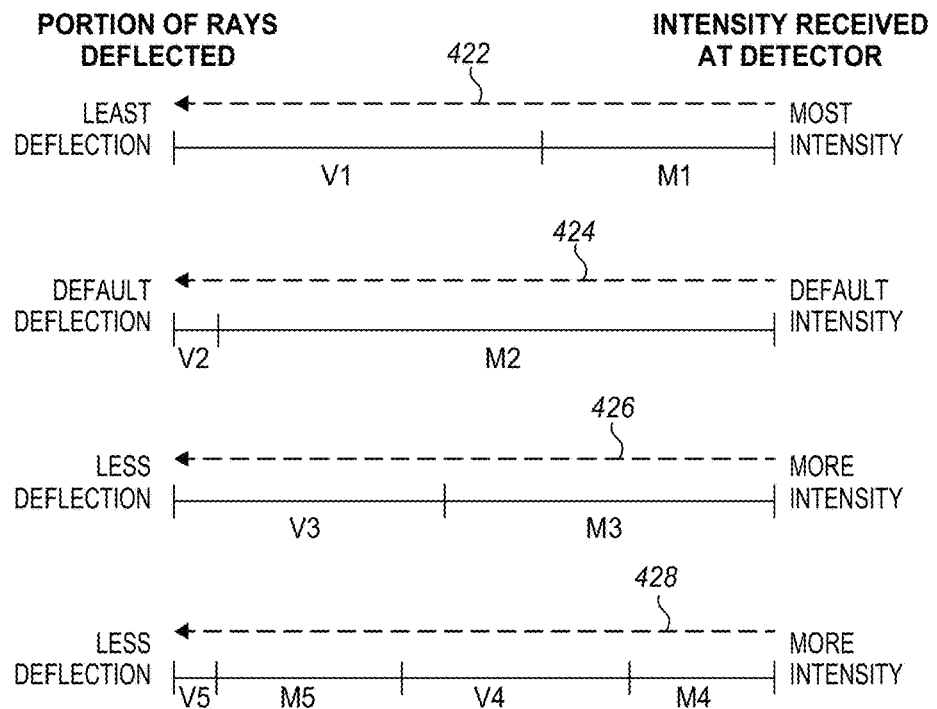
FIG. 5 is a diagram illustrating sidescatter radiation of FIG. 4 passing through material and voids (e.g., resulting from a delamination) in an exemplary embodiment.

FIG. 5 is a diagram illustrating sidescatter radiation of FIG. 4 passing through material (M) and voids (V) (e.g., resulting from a delamination) in an exemplary embodiment. Since the intensity of sidescatter radiation (and indeed, any x-ray beam) attenuates as it passes through material, the presence of a delamination may be inferred at locations where sidescatter radiation passes through the least amount of material and hence is most intense. In FIG. 5, x-ray 422 passes through void V1 and material M1, x-ray 424 passes through void V2 and material M2, x-ray 426 passes through void V3 and material M3, and x-ray 428 passes through voids V4 and V5 as well as material M4 and M5. Since x-ray 422 passes through the most void and the least material, it attenuates the least and hence has a greater intensity than other sidescatter radiation. In contrast, x-ray 424 passes through the most material possible on its direct path to x-ray detector 340, and therefore attenuates the most. X-rays 426 and 428 pass through more material than x-ray 422, but less material than x-ray 424, and hence attenuate by an amount in between that of x-ray 422 and x-ray 424. Controller 350, by analyzing differences in received intensity of radiation received at different locations along Z, may detect areas of increased intensity, and infer the presence of delaminations based on this difference in intensity.

Figure 6:
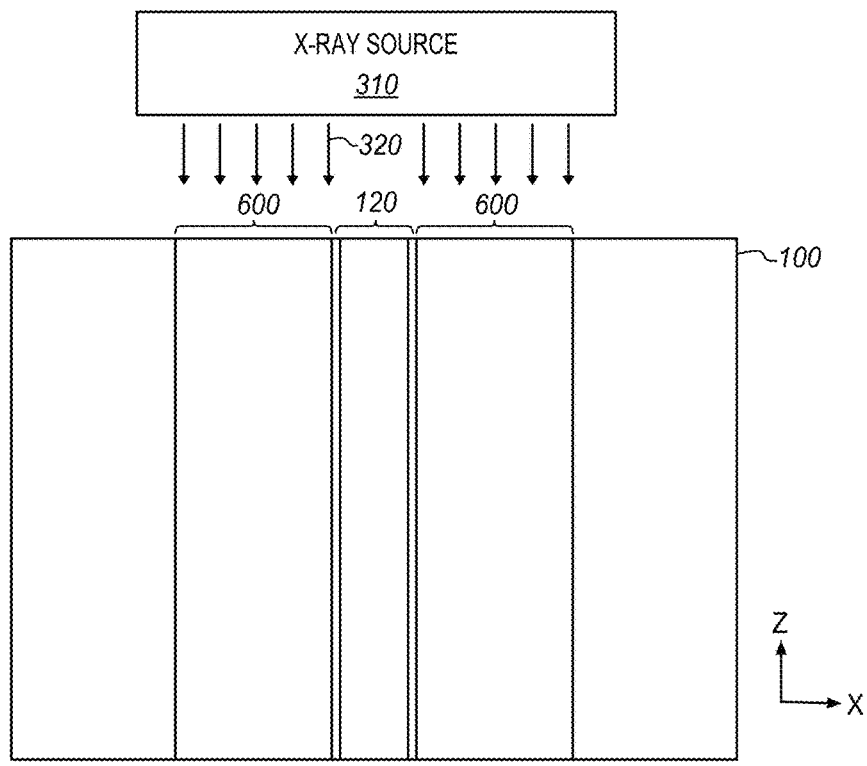
FIG. 6 is a diagram illustrating a side view of a region of a composite part struck by an x-ray beam in an exemplary embodiment.

FIG. 6 is a diagram illustrating a side view of a region of a composite part struck by an x-ray beam 320 in an exemplary embodiment. FIG. 6 illustrates an embodiment wherein no radiation shield 330 is used to prevent beam 320 of x-rays from directly striking x-ray detector 340. Instead, beam 320 is shaped (e.g., by a optics or another component) to strike composite part 100 only in area 600, which forms a concentric ring that surrounds but does not overlap hole 120.

Illustrative details of the operation of sidescatter imaging system 300 will be discussed with regard to FIG. 7. Assume, for this embodiment, that a technician wishes to inspect a CFRP sample (e.g., part 100). Thus, the technician places x-ray source 310 in a location where x-ray source 310 will radiate x-rays through multiple layers of part 100. The technician further orients x-ray detector 340 to extend along a firing direction (e.g., a thickness of part 100 along the Z direction) in order to capture sidescatter radiation at a variety of locations along x-ray detector 340.

Figure 7:
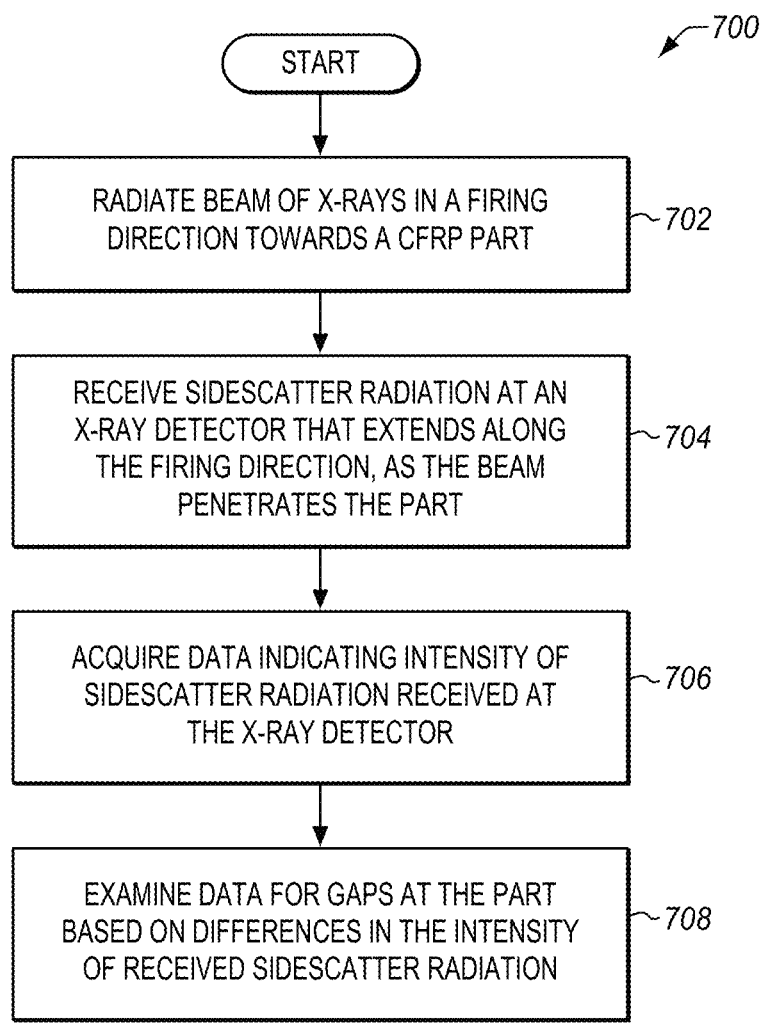
FIG. 7 is a flowchart illustrating a method for operating a sidescatter x-ray imaging system to inspect a composite part in an exemplary embodiment.

FIG. 7 is a flowchart illustrating a method 700 for operating sidescatter imaging system 30 in an exemplary embodiment. The steps of method 700 are described with reference to system 300 of FIG. 3, but those skilled in the art will appreciate that method 400 may be performed in other systems. The steps of the flowcharts described herein are not all inclusive and may include other steps not shown. The steps described herein may also be performed in an alternative order.

Controller 350 operates x-ray source 310 to radiate beam 320 of x-rays in firing direction F towards surface 110 and through part 100 (step 702). As beam 320 travels through material within part 100, beam 320 attenuates due to the reflection of x-rays, resulting in sidescatter radiation 322. Sidescatter radiation 322 travels horizontally through part 100, eventually striking x-ray detector 340. X-ray detector 340 receives sidescatter radiation 322 as beam 320 penetrates part 100 (step 704). X-ray detector 340 further generates intensity data based on received amounts of sidescatter radiation 322 at X-ray detector 340, and controller 350 acquires the data (step 706). In embodiments where x-ray detector 340 is placed at side 130 of part 100, x-ray detector 340 may generate intensity data for a flat two-dimensional surface (e.g., the YZ plane) corresponding to side 130. In embodiments where x-ray detector 340 is placed within hole 120, x-ray detector 340 may generate intensity data for a curved two-dimensional surface (e.g., a cylindrical surface corresponding with the boundary of hole 120). This results in intensity data which may be stored in controller 350 in memory.

Controller 350 examines the data for gaps 410 and 412 (e.g., delaminations between layers) at part 100 based on differences in the intensity of received sidescatter radiation at x-ray detector 340 (step 708). For example, controller 350 may analyze the stored intensity data in order to detect notable differences in sidescatter radiation intensity along the thickness of part 100. In locations along the thickness that exhibit increased intensity with respect to neighboring regions, controller 350 may infer that a delamination, void, or other gap exists. Controller 350 may further detect any suitable deformity, such as trapped air pockets, gas bubbles, or voids that are not found at the border between two layers. In short, controller 350 engages in non-destructive inspection via x-rays, and may determine whether a void or delamination exists based on the intensity of x-rays captured by sensor 340.

Figure 8:
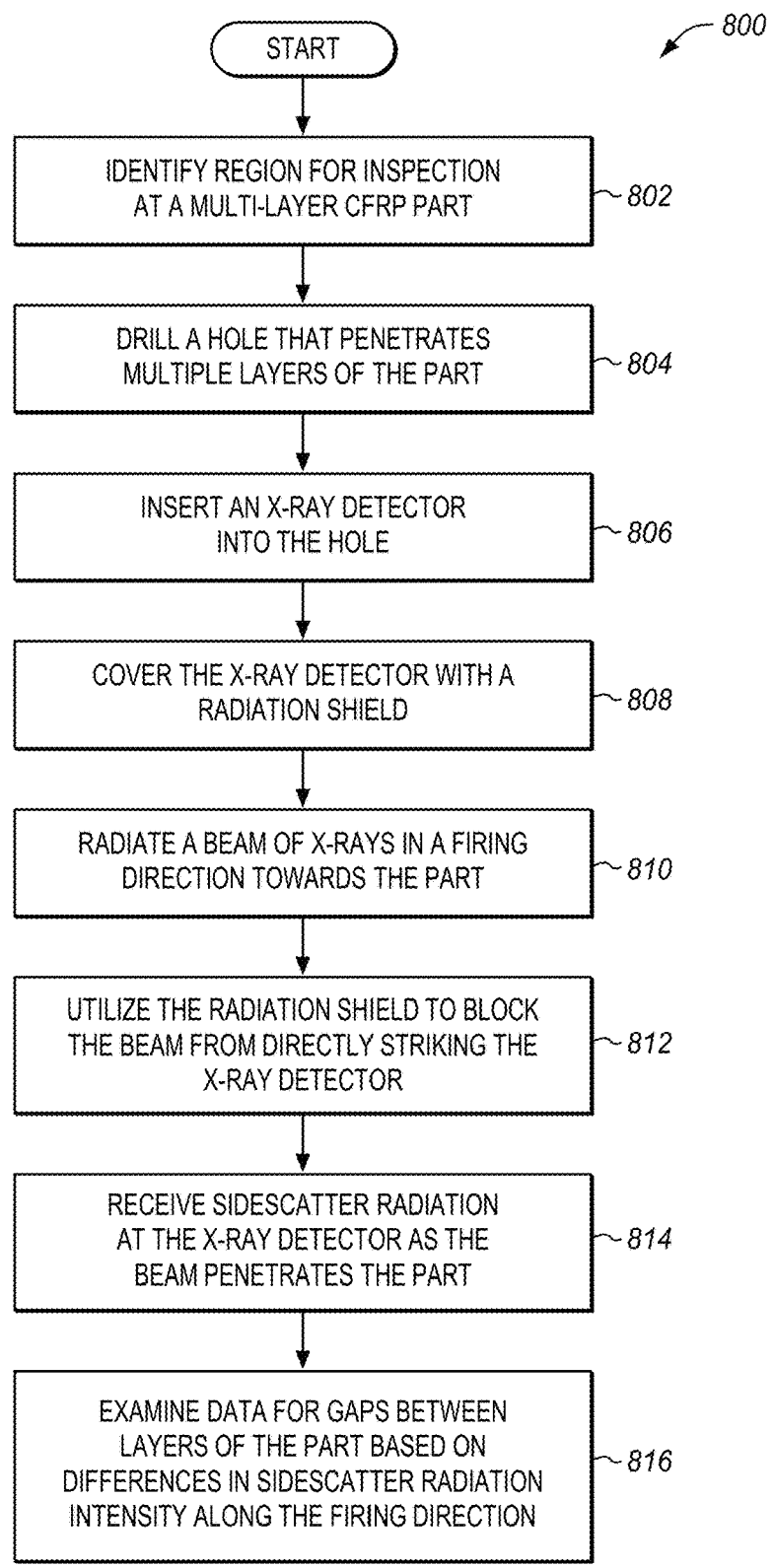
FIG. 8 is a flowchart illustrating a further method for inspecting a composite part via sidescatter x-rays in an exemplary embodiment.

FIG. 8 is a flowchart illustrating a method 800 for inspecting a composite part 100 in an exemplary embodiment. Unlike method 700 which describes a technique for engaging in nondestructive testing, method 800 of FIG. 8 illustrates a method of destructive testing. These techniques may be useful when attempting to detect delaminations in a region of a composite part that is not close to a side 130 or a hole 120 at the composite part. Specifically, these techniques ensure that sidescatter radiation 322 received at x-ray detector 340 is not overly attenuated by travel across substantial lengths (e.g., entire meters) of composite material.

Method 800 includes identifying a region for inspection at part 100 (step 802). This may comprise identifying a region that is suspected of having a delamination or a void, or identifying a region that has not been inspected for delaminations for some threshold period of time. As used herein, a "region" of part 100 comprises any suitable portion of part 100 extending along the thickness of part 100 and comprising at least one square centimeter of area in the XY plane. A hole is then drilled that penetrates multiple layers of part 100 in the region (step 804). The drilling of hole 120 comprises the destructive part of method 800. This operation may be performed by a technician, or by a robot in accordance with a Numerical Control (NC) program. The hole may, for example, penetrate through the entirety of the thickness of part 100. An x-ray detector 340 is inserted into the hole (step 806), and the x-ray detector is covered with radiation shield 330 (step 808). X-ray source 310 radiates beam 320 of x-rays in firing direction F (step 810), and radiation shield 330 blocks x-rays in beam 320 that would directly strike x-ray detector 340 (step 812). Sidescatter radiation 322 is received at x-ray detector 340 as beam 320 penetrates part 100 (step 814), and intensity data indicating the strength of received sidescatter radiation 322 is stored in memory at controller 350. Controller 350 further proceeds to examine the data for gaps 410-414 between layers 210 of part 100, based on differences in sidescatter radiation intensity along the firing direction F (step 816). Drilling a hole and testing in this manner is a quicker and a less destructive means of inspecting the interior of a laminate than was previously available, in that one small hole may be used to inspect the contents of an entire region of a composite part.

Figure 9:
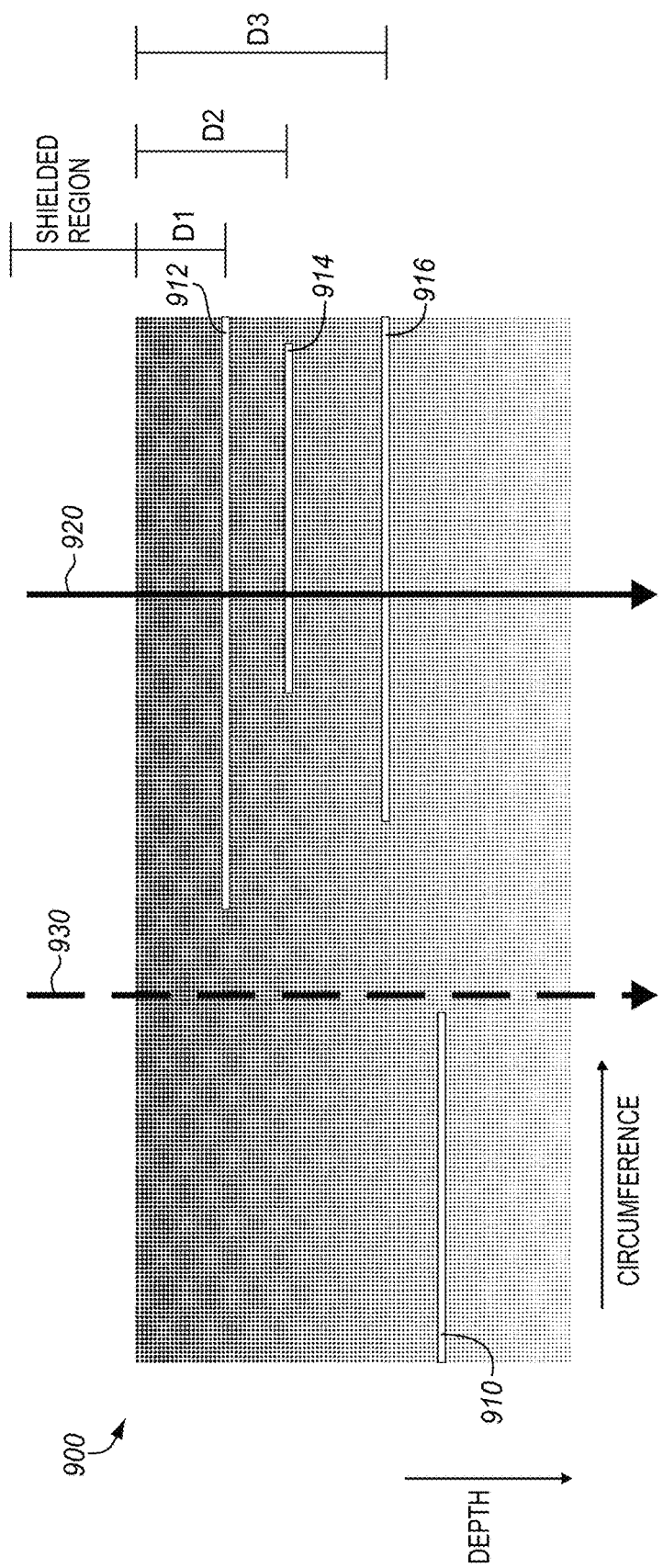
FIG. 9 is a diagram illustrating an image generated by a sidescatter x-ray imaging system in an exemplary embodiment.

FIG. 9 is a diagram illustrating an image 900 generated by sidescatter x-ray imaging system 300 in an exemplary embodiment. Areas of greater intensity are darker than areas of lesser intensity. Thus, image 900, which is cylindrical in nature and has been detected by sensor 340, has been laid flat in planar form for viewing. In this manner, one edge would mate to another edge when image 900 is re-formed into a cylinder. In this embodiment, x-ray detector 340 comprises a circumferential x-ray detector placed into a hole 120, and x-ray source 310 radiates a beam 320 of x-rays that surrounds hole 120. Thus, image 900 illustrates measured sidescatter x-ray intensity (e.g., magnitude of received energy) along both the depth and circumference of hole 120. Image 900 includes multiple bands 910, 912, 914, and 916 which have increased intensity with respect to neighboring locations. This results in a notable contrast between bands 910-916 and the rest of image 900. These bands 910-916 correspond with delaminations in part 100.

In this embodiment, band 912 is increased in intensity due to gap 410 detected by x-ray 422, band 914 is increased in intensity due to gap 412 detected by x-ray 424, and band 916 is increased in intensity due to gap 414 detected by x-ray 428. That is, bands 912-916 exhibit increased intensity on image 900, because the x-rays that generated these bands passed through less material and hence were attenuated less prior to sensing than other x-rays. Band 910 has increased intensity for a similar reason. When image 900 is analyzed at a specific position along the circumference of the hole, delaminations and/or voids may be detected at that circumferential location. For example, line 930 passes through no bands of increased intensity, indicating that its circumferential location at hole 120 has no delaminations or voids. In contrast, line 920 passes through three bands 912, 914, and 916 of increased intensity, meaning that three delaminations and/or voids are located at the circumferential location of line 920. Hence, the location of line 920 along the circumference of hole 120 corresponds with three different delaminations at three different depths (corresponding with D1, D2, and D3) within hole 120.

Figure 10:
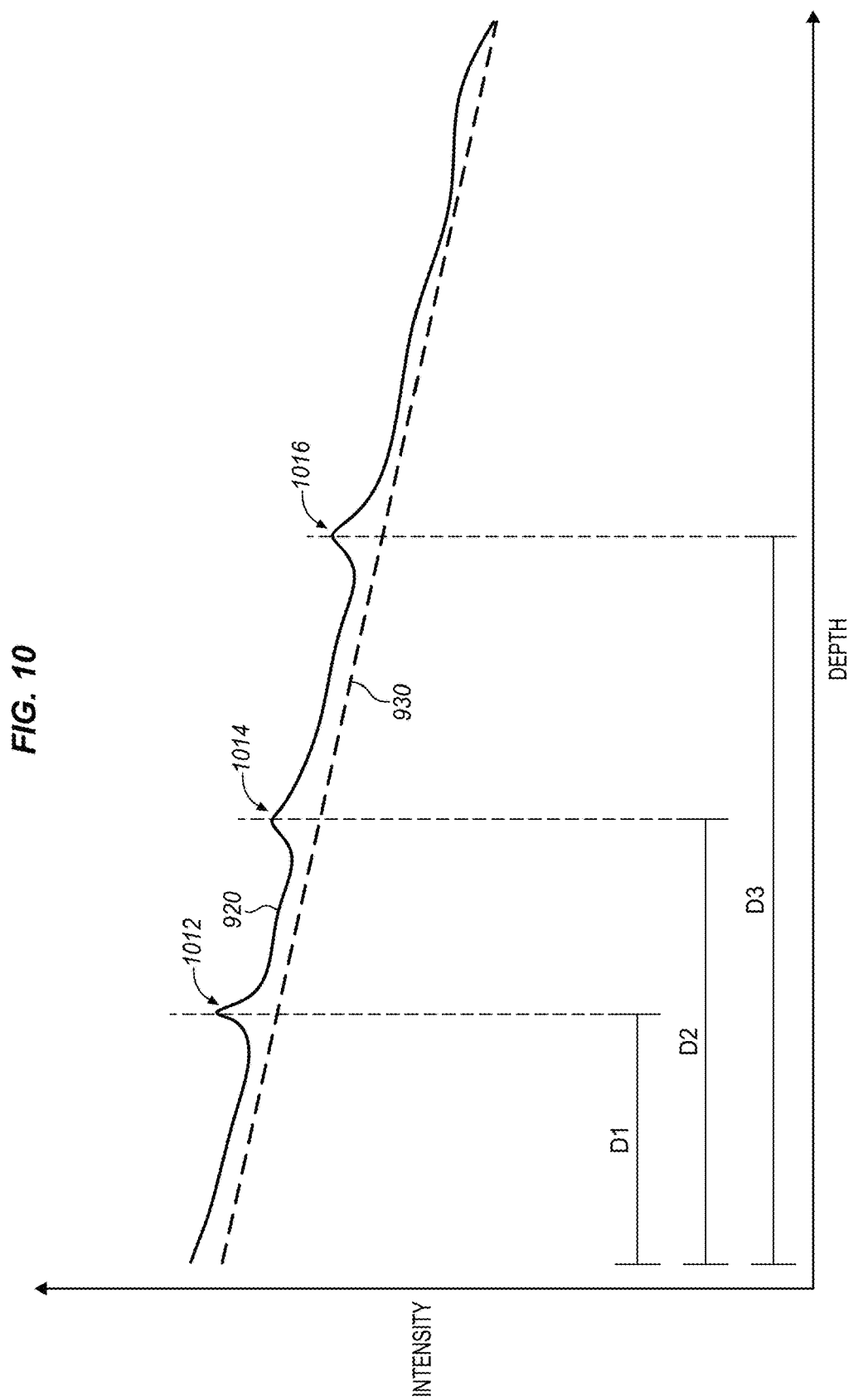
FIG. 10 is a diagram illustrating lines of the image of FIG. 9 in an exemplary embodiment.

FIG. 10 is a diagram illustrating lines of the image of FIG. 9 in an exemplary embodiment. According to FIG. 10, line 930 attenuates in intensity as depth increases, because x-rays traverse more material within part 100 before reaching deeper depths, resulting in further attenuation. Since no bands of increased intensity are traversed by line 930, line 930 decreases in intensity in a uniform fashion. In contrast to line 930, line 920 exhibits multiple peaks of intensity 1012, 1014, and 1016 (corresponding with depths D1, D2, and D3) in received sidescatter radiation. These peaks occur with respect to neighboring regions even though line 930 also decreases in intensity with depth. Thus, the peaks in received sidescatter radiation data may indicate the presence of gaps between layers. Controller 350 may therefore numerically detect the specific depths of delaminations in part 100 by measuring the slope of line 920 as depth increases, and detecting depths at which the slope changes from a positive value to a negative one.

EXAMPLES

In the following examples, additional processes, systems, and methods are described in the context of a sidescatter x-ray imaging system.

Figure 11:
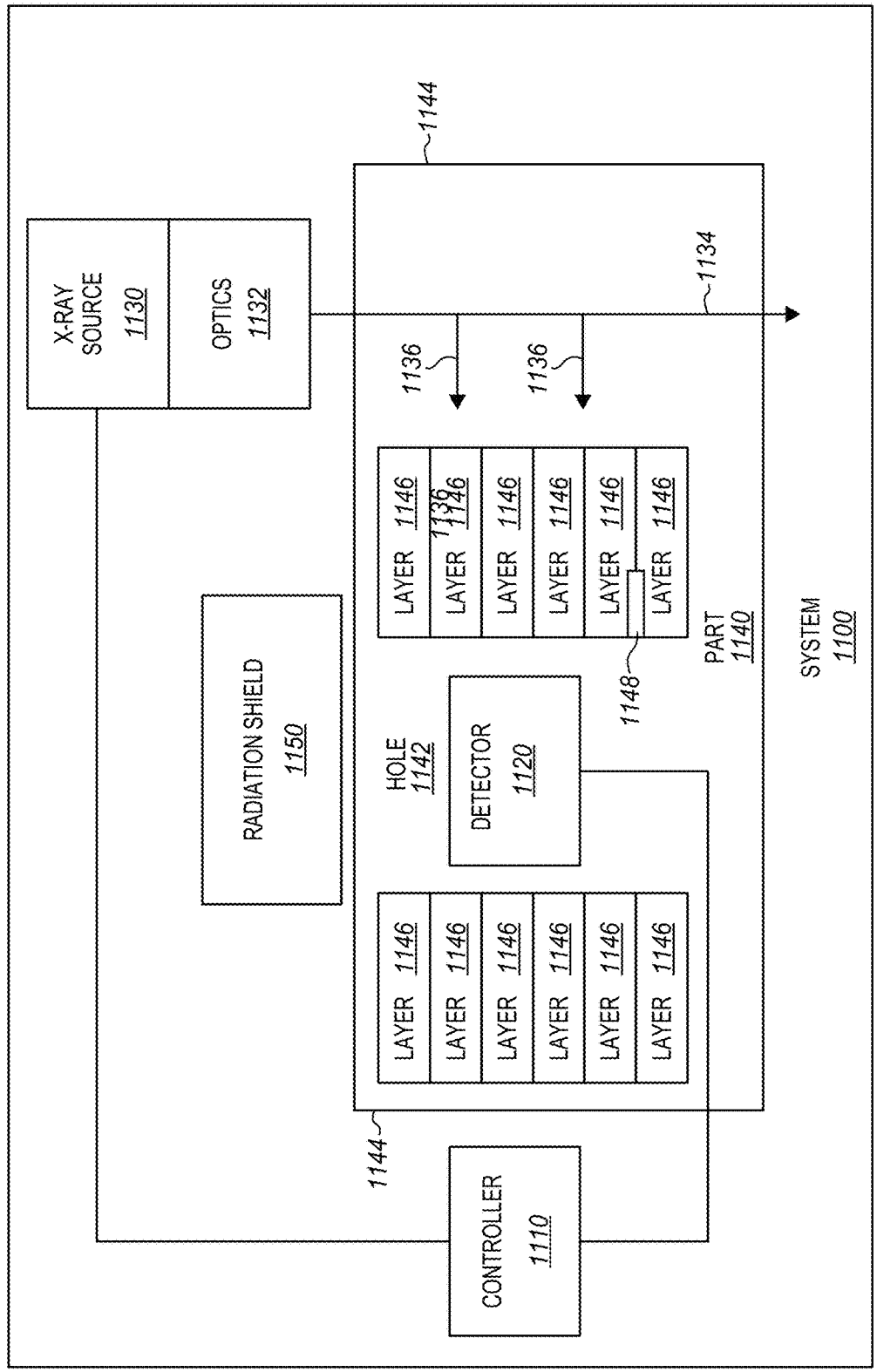
FIG. 11 is a block diagram of a sidescatter x-ray imaging system in an exemplary embodiment.

FIG. 11 is a block diagram of a sidescatter x-ray imaging system 1100 in an exemplary embodiment. According to FIG. 11, system 1100 includes controller 1110, detector 1120, and x-ray source 1130. X-ray source 1130 includes optics 1132, which shape beam 1134 of x-rays that radiate from x-ray source 1130. Radiation shield 1150 prevents beam 320 from directly striking detector 1120. This ensures that detector 1120 only detects sidescatter radiation 1136 from x-ray source 1130. Sidescatter radiation 1136 proceeds through layers 1146 of part 1140, eventually reaching hole 1142 and striking detector 1120. Some sidescatter radiation travels through empty volumes of space which correspond with delamination 1148, and therefore exhibit less attenuation (and therefore higher intensity) when they strike detector 1120. Controller 1110 manages the operations of detector 1120 and x-ray source 1130. For example, controller 1110 may operate optics 1132 in order to shape beam 1134, and may perform signal gating operations at detector 1120 to ensure that detector detects synchronously with the radiation of x-rays from x-ray source 1130. In this FIG. although part 1140 is illustrated as being within system 1100, part 1140 is not a component of system 1100 but rather is being inspected by system 1100.

Figure 12:
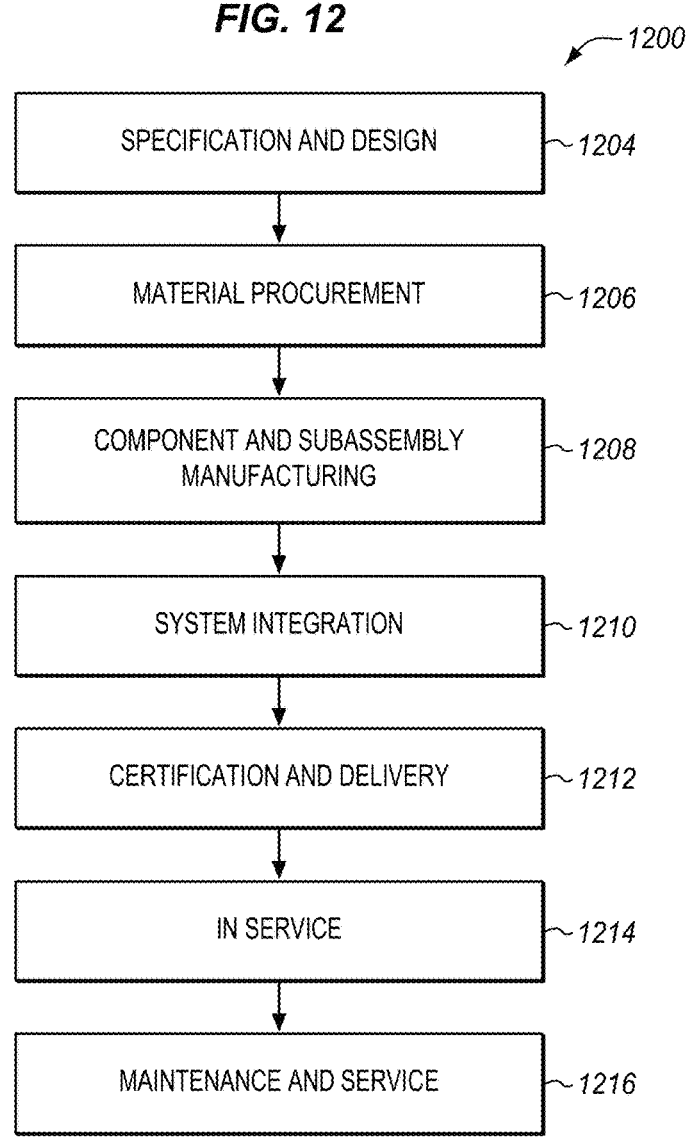
FIG. 12 is a flow diagram of aircraft production and service methodology in an exemplary embodiment.
Figure 13:
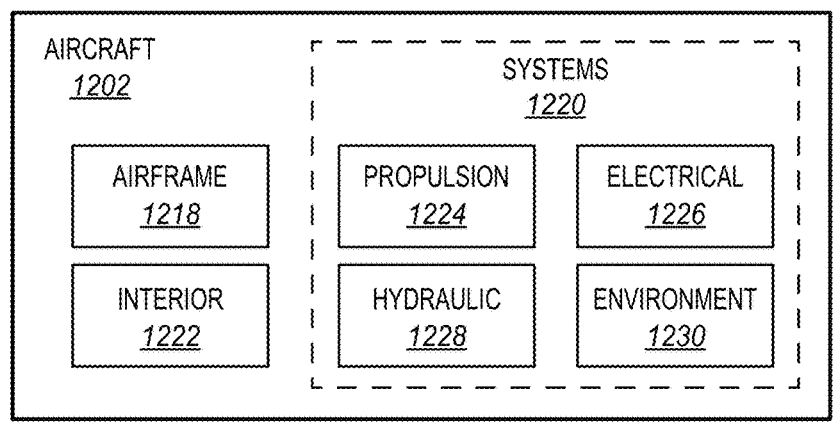
FIG. 13 is a block diagram of an aircraft in an exemplary embodiment.

Referring more particularly to the drawings, embodiments of the disclosure may be described in the context of an aircraft manufacturing and service method 1200 as shown in FIG. 12 and an aircraft 1202 as shown in FIG. 13. During pre-production, exemplary method 1200 may include specification and design 1204 of the aircraft 1202 and material procurement 1206. During production, component and subassembly manufacturing 1208 and system integration 1210 of the aircraft 1202 takes place. Thereafter, the aircraft 1202 may go through certification and delivery 1212 in order to be placed in service 1214. While in service by a customer, the aircraft 1202 is scheduled for routine maintenance and service 1216 (which may also include modification, reconfiguration, refurbishment, and so on). Apparatus and methods embodied herein may be employed during any one or more suitable stages of the production and service method 1200 (e.g., specification and design 1204, material procurement 1206, component and subassembly manufacturing 1208, system integration 1210, certification and delivery 1212, service 1214, maintenance and service 1216) and/or any suitable component of aircraft 1202 (e.g., airframe 1218, systems 1220, interior 1222, propulsion 1224, electrical 1226, hydraulic 1228, environmental 1230).

Each of the processes of method 1200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 13, the aircraft 1202 produced by exemplary method 1200 may include an airframe 1218 with a plurality of systems 1220 and an interior 1222. Examples of high-level systems 1220 include one or more of a propulsion system 1224, an electrical system 1226, a hydraulic system 1228, and an environmental system 1230. Any number of other systems may be included. Although an aerospace example is shown, the principles of the invention may be applied to other industries, such as the automotive industry.

As already mentioned above, apparatus and methods embodied herein may be employed during any one or more of the stages of the production and service method 1200. For example, components or subassemblies corresponding to production stage 1208 may be fabricated or manufactured in a manner similar to components or subassemblies produced while the aircraft 1202 is in service. Also, one or more apparatus embodiments, method embodiments, or a combination thereof may be utilized during the production stages 1208 and 1210, for example, by substantially expediting assembly of or reducing the cost of an aircraft 1202. Similarly, one or more of apparatus embodiments, method embodiments, or a combination thereof may be utilized while the aircraft 1202 is in service, for example and without limitation, to maintenance and service 1216. For example, the techniques and systems described herein may be used for steps 1202, 1206, 1208, 1210, 1212, 1214, and/or 1216, and/or may be used for airframe 1218 and/or interior 1222. These techniques and systems may even be utilized for systems 1220, including for example propulsion 1224, electrical 1226, hydraulic 1228, and/or environmental 1230.

In one embodiment, part 100 comprises a portion of an airframe, and is manufactured during component and subassembly manufacturing 1208. Part 100 may then be assembled into an aircraft in system integration 1210, when it is inspected via sidescatter x-ray imaging system 300. Part 100 may then be utilized in service 1214 until it undergoes a certain amount of wear, at which time imaging system 300 may be utilized again to inspect part 100, via destructive or nondestructive tests.

Any of the various control elements (e.g., electrical or electronic components) shown in the figures or described herein may be implemented as hardware, a processor implementing software, a processor implementing firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller"

should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, a control element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

The invention claimed is:

1. A method comprising:
radiating a beam of x-rays in a firing direction towards surface of a multi-layer Carbon Fiber Reinforced Polymer (CFRP) part;
acquiring data indicating intensity of sidescatter radiation received at an x-ray detector that extends along the CFRP part in the firing direction; and
examining the acquired data from the x-ray detector for gaps at the CFRP part based on differences between intensities detected by the x-ray detector at different locations along a dimension of the part.

2. The method of claim 1 further comprising:
placing the x-ray detector within a hole at the part, the hole extending across multiple layers, wherein the part is aligned such that the hole extends in the firing direction.

3. The method of claim 1 wherein:
radiating the beam results in the beam striking an area surrounding the hole; and
the x-ray detector engages in receiving sidescatter radiation along an entire circumference of the x-ray detector.

4. The method of claim 1 further comprising:
radiating the beam of x-rays in the firing direction via an x-ray source.

5. The method of claim 1 wherein:
the gaps comprise delaminations or voids between layers of the CFRP part.

6. The method of claim 1 further comprising:
interposing a radiation shield between the x-ray detector and an x-ray source, thereby blocking the beam from directly striking the x-ray detector.

7. The method of 1 further comprising:
placing the x-ray detector along a side of the part that extends in the firing direction.

8. The method of claim 1 further comprising:
identifying locations at the x-ray detector that have received amounts of sidescatter radiation that are higher than a threshold; and
determining that the locations correspond with gaps within the CFRP part.

9. The method of claim 1 further comprising:
identifying peaks in received sidescatter radiation along the firing direction; and
determining that the peaks indicate the presence of gaps in the CFRP part.

10. A method comprising:
identifying a region for inspection at a multi-layer Carbon Fiber Reinforced Polymer (CFRP) part;
drilling a hole that penetrates multiple layers of the CFRP part in the region;
inserting an x-ray detector into the hole;
radiating a beam of x-rays in the firing direction;
receiving sidescatter radiation at an x-ray detector as the beam penetrates the CFRP part;
acquiring data indicating intensity of sidescatter radiation received at the x-ray detector; and
examining the acquired data for gaps at the CFRP part based on differences in intensity indicated by the data.

11. The method of claim 10 further comprising:
utilizing a radiation shield to block the beam from directly striking the x-ray detector.

12. The method of claim 10 wherein:
radiating the beam results in the beam striking an area surrounding the hole; and
receiving sidescatter radiation at the x-ray detector comprises receiving sidescatter radiation along an entire circumference of the x-ray detector.

13. The method of claim 10 further comprising:
identifying locations at the x-ray detector that have received amounts of sidescatter radiation that are higher than a threshold; and
determining that the locations correspond with gaps between layers of the CFRP part.

14. The method of claim 10 further comprising:
identifying peaks in received sidescatter radiation along the firing direction; and
determining that the peaks indicate the presence of gaps in the CFRP part.

15. A system comprising:
an x-ray source that radiates a beam of x-rays in a firing direction towards a surface of a multi-layer Carbon Fiber Reinforced Polymer (CFRP) part for inspection;
an x-ray detector at the CFRP part that extends along the firing direction and receives sidescatter radiation as the beam penetrates the CFRP part; and
a controller that acquires data generated by the x-ray detector, and examines the acquired data for differences between intensities detected by the x-ray detector at different locations along a dimension of the part.

16. The system of claim 15 further comprising:
a radiation shield, interposed between the x-ray detector and the x-ray source, that blocks the beam from directly striking the x-ray detector.

17. The system of claim 15 further comprising:
the CFRP part, wherein the x-ray detector is placed along a side of the CFRP part that extends in the firing direction.

18. The system of claim 15 further comprising:
the CFRP part, wherein the x-ray detector is placed within a hole at the CFRP part, the hole extends across multiple layers, and the CFRP part is aligned such that the hole extends in the firing direction.

19. The system of claim 18 wherein:
the beam strikes an area surrounding the hole; and
the x-ray detector receives sidescatter radiation along an entire circumference of the x-ray detector.

20. The system of claim 15 wherein:
the controller identifies locations at the x-ray detector that have received amounts of sidescatter radiation that are higher than a threshold, and determines that the locations correspond with gaps between layers of the part.

21. The system of claim 15 wherein:
the detector comprises a digital x-ray detector.

22. The system of claim 15 wherein:
the controller identifies peaks in received sidescatter radiation along the firing direction, and determines that the peaks correspond with gaps between layers of the part.

23. The system of claim 15 wherein:
the detector comprises a circumferential x-ray detector.

* * * * *